United States Patent [19]

Spano et al.

[11] Patent Number: 5,797,965
[45] Date of Patent: Aug. 25, 1998

[54] SUPPRESSION OF EPILEPTIFORM ACTIVITY

[75] Inventors: Mark L. Spano, Laurel; Steven J. Schiff, Rockville, both of Md.; Bruce J. Gluckman, Arlington, Va.; William L. Ditto, Woodstock, Ga.

[73] Assignee: The United States of America as represented by the Secretary of the Navy, Washington, D.C.

[21] Appl. No.: 825,150

[22] Filed: Mar. 26, 1997

Related U.S. Application Data

[60] Provisional application No. 60/018,606 May 30, 1996.

[63] Continuation-in-part of Ser. No. 299,999, Aug. 19, 1994, Pat. No. 5,522,863.

[51] Int. Cl.⁶ ............................................. A61N 1/18

[52] U.S. Cl. .............................................. 607/2; 607/45
[58] Field of Search ................................ 607/45, 46, 72, 607/74, 2, 116, 118; 600/544, 545

[56] References Cited

U.S. PATENT DOCUMENTS

| | | | |
|---|---|---|---|
| 3,850,161 | 11/1974 | Liss | 607/63 |
| 5,299,569 | 4/1994 | Wernicke et al. | 607/45 |
| 5,411,540 | 5/1995 | Edell et al. | 607/53 |
| 5,522,863 | 6/1996 | Spano et al. | 607/72 |

Primary Examiner—Jeffrey R. Jastrzab
Attorney, Agent, or Firm—John Forrest; Jacob Shuster

[57] ABSTRACT

A DC electric field is applied to brain tissue in parallel alignment with neurons thereof during periods of brief duration while the tissue is undergoing epileptic activity. The electrical field is controllably varied in magnitude to suppress such epilieptic activity.

10 Claims, 4 Drawing Sheets

SUPPRESSION OF EPILEPTIFORM ACTIVITY

The present invention relates in general to monitoring, analyzing and modifying behavior of a neural network, and is related to subject matter presented in a prior application, Ser. No. 08/299,999 filed Aug. 19,1994, now U.S. Pat. No. 5,522,863 to Spano et al. with respect to which the present application is a continuation-in-part and the disclosure of which is incorporated herein by reference.

The present invention claims benefit of provisional application Ser. No. 60/018,606 filed May 30, 1996.

BACKGROUND OF THE INVENTION

Modification of epileptic foci in the neuronal networks of living brain tissue is referred to in the aforementioned U.S. Pat. No. 5,522,863 to Spano et al. It is also known from biological studies made that electric fields affect neuronal activity when aligned with brain tissue to vary neuron excitability therein or the threshold for initiation of nerve action potentials. Physiological activities similar to epileptiform activity are also known to occur in brain tissue from studies on hippocompal tissue slices exposed to a persuate having an elevated potassium content. Based on the foregoing studies, it is an important object of the present invention to non-invasively effect in-vivo suppression of epileptiform activity arising in the neuronal network of brain tissue or the like because of nervous system disorders.

SUMMARY OF THE INVENTION

In accordance with the present invention, the hippocampal portion of brain tissue is exposed to DC electric fields generated between electrodes to which symmetric balancing potentials are applied in order to minimize absolute change in potential applied by the electric field which is aligned with the brain tissue within which epileptic activity is induced. Electric fields are accordingly established parallel to brain tissue neurons at low levels during periods of brief duration in accordance with a program based on a system-wide parameter for pacing and entrainment of epileptic focus, or complete suppression of the epileptic activity being monitored.

BRIEF DESCRIPTION OF DRAWING FIGURES

A more complete appreciation of the invention and many of its attendant advantages will be readily appreciated as the same becomes better understood by reference to the following detailed description when considered in connection with the accompanying drawing wherein.

DETAILED DESCRIPTION OF PREFERRED EMBODIMENTS

As disclosed in U.S. Pat. No. 5,522,863 to Spano et al. a slice of brain tissue obtained from the hippocompus of the temporal lobe, is perfused with fluid containing potassium within an exposure chamber. The anatomy of such brain tissue includes a collateral fiber tract connected to pyramidal neurons at Cormu Ammonis (CA) regions. The perfusate fluid within which such brain tissue is submerged, is changed by increase in ionic concentration of the potassium to 8.5 mMK in order to induce epileptic activity reflected by system characterizing events in the form of spontaneous bursts from the two regions (CA1 and CA3) at opposite ends of the collateral fiber tract.

Figure 1:
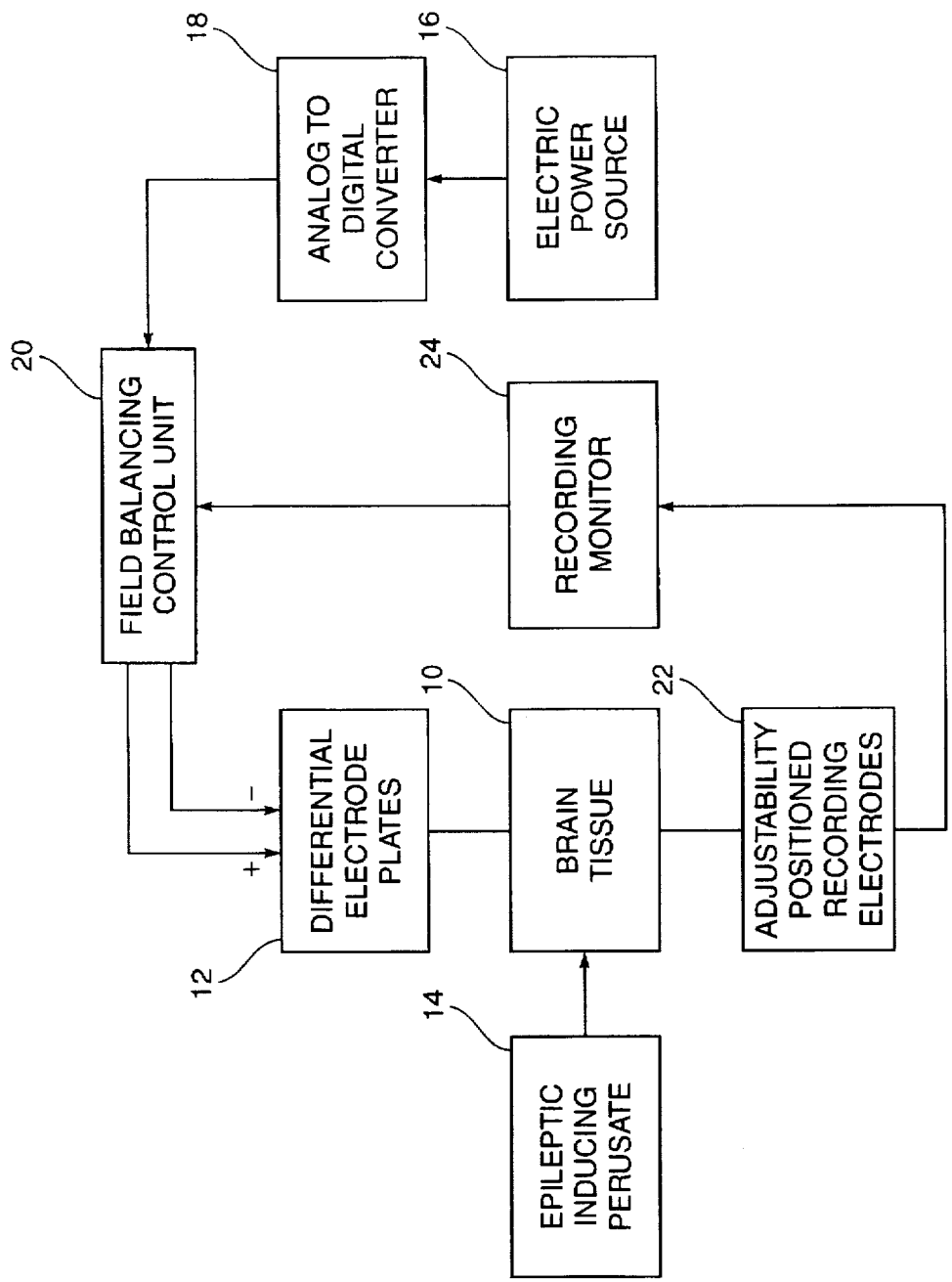
FIG. 1 is a block diagram of apparatus and components of a system associated with a neuronal network in accordance with the present invention.
Figure 2A:
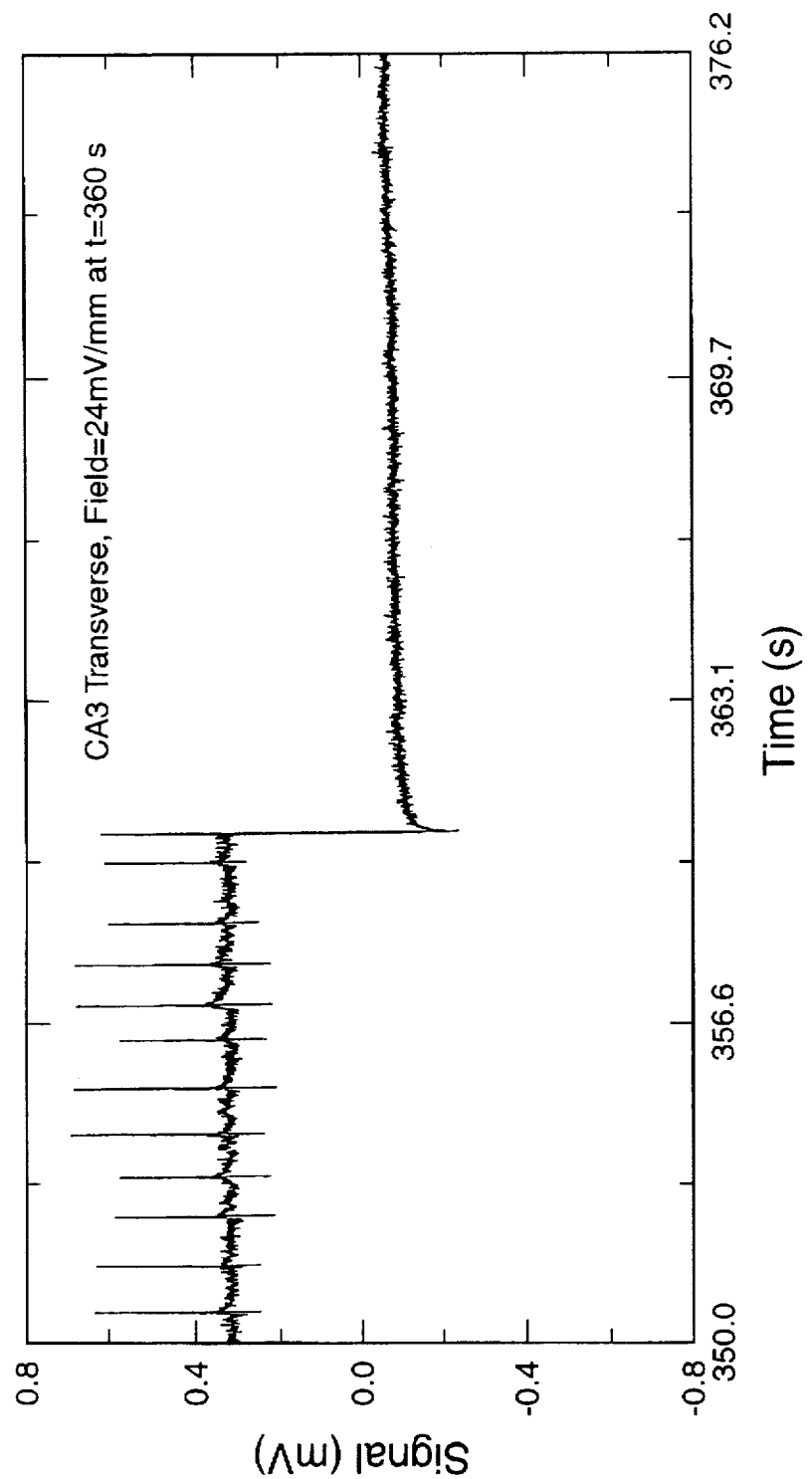
FIGS. 2A and 2B are graphical plots of neuronal activity of brain tissue subject to behavior control by the system depicted in FIG. 1.
Figure 2B:
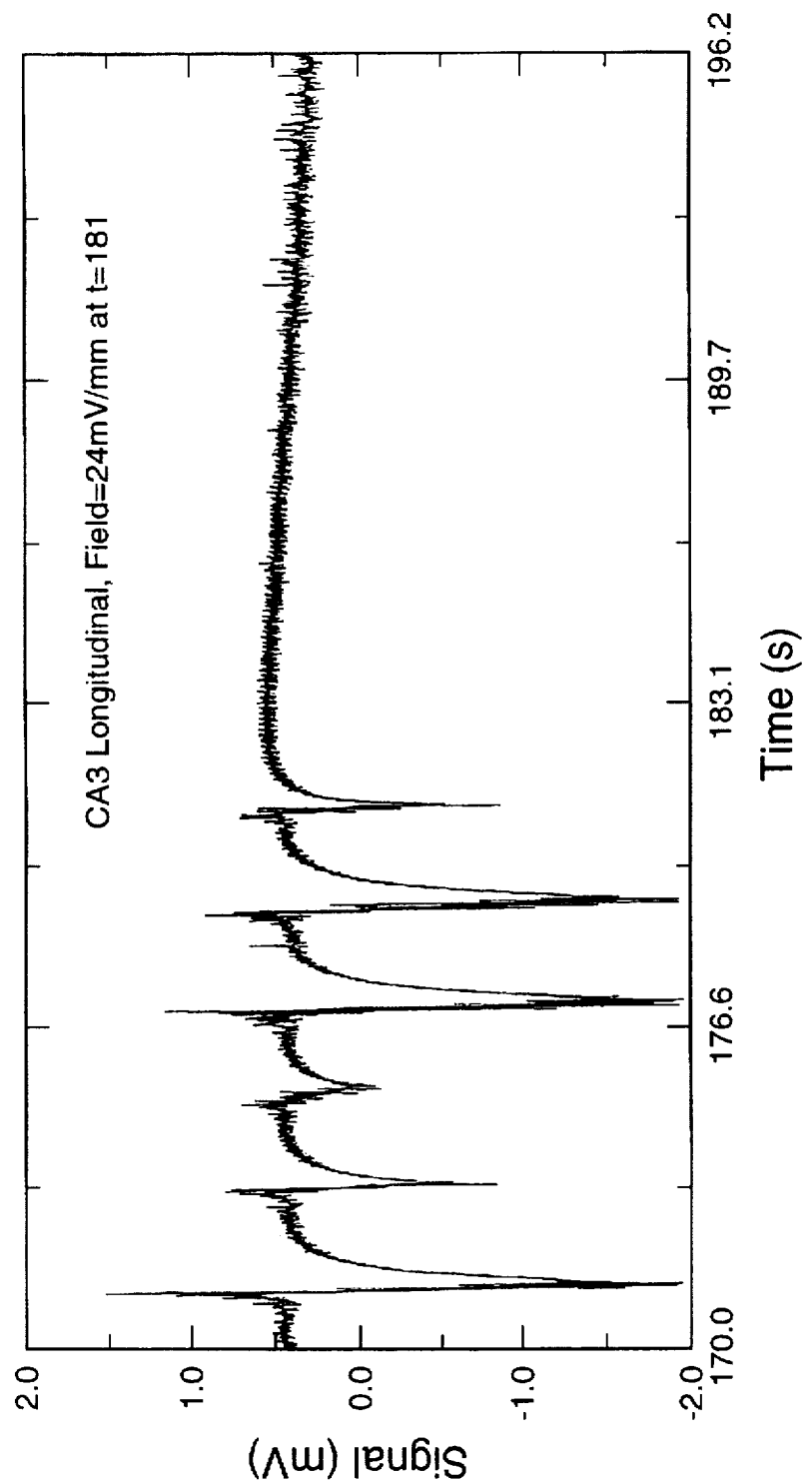

Pursuant to the present invention, an electric field aligned parallel to the aforementioned pyramidal neurons of brain tissue 10, as denoted in FIG. 1, is established between two Ag-AgCl electrode plates 12 separated by a distance of 2 cm while submerged in perfusate fluid 14 to induce epileptic activity. As also diagrammed in FIG. 1, a power source 16 is connected through analog-to-digital converter 18 to a field balancing control unit 20 from which symmetric positive and negative potentials are respectively applied to the differential electrode plates 12 in order to minimize potential change at the center of the perfusate fluid chamber within which the slices of brain tissue 10 are aligned with the electric field. Saline filled glass micropipette recording electrodes 22 are adjustably positioned within the brain tissue and within the perfusate fluid chamber adjacent the brain tissue slices. By adjustment of the recording electrode position and control of the field balancing potentials applied to the differential electrode plates, recordation of burst discharges reflecting neuronal activity was reliably achieved by the recording monitor 24 despite large field changes as reflected by the graphical plots of FIGS. 2A and 2B. FIG. 2A graphically illustrates neuronal pulsating activity in the form of burst discharges from a CA3 region of a transversely cut slice of brain tissue, before and after switching of an aligned electric field between high and low magnitude by the control unit 20. In such CA3 region the burst-firing activity generated is similar to human interictal spikes while the activity generated in the CA1 region was more prolonged seizure-like events. FIG. 2B also graphically illustrates the affect of field magnitude change at the CA3 region on a longitudinally cut slice of the brain tissue, as part of the available evidence that epileptiform activity may be suppressed by electric fields of relatively small magnitude established for periods of short duration in accordance with a desired behavior modifying program based on variations of a chaos controlling algorithm applicable to neural networks as referred to in U.S. Pat. No. 5,522,863 to Spano et al.

Figure 3:
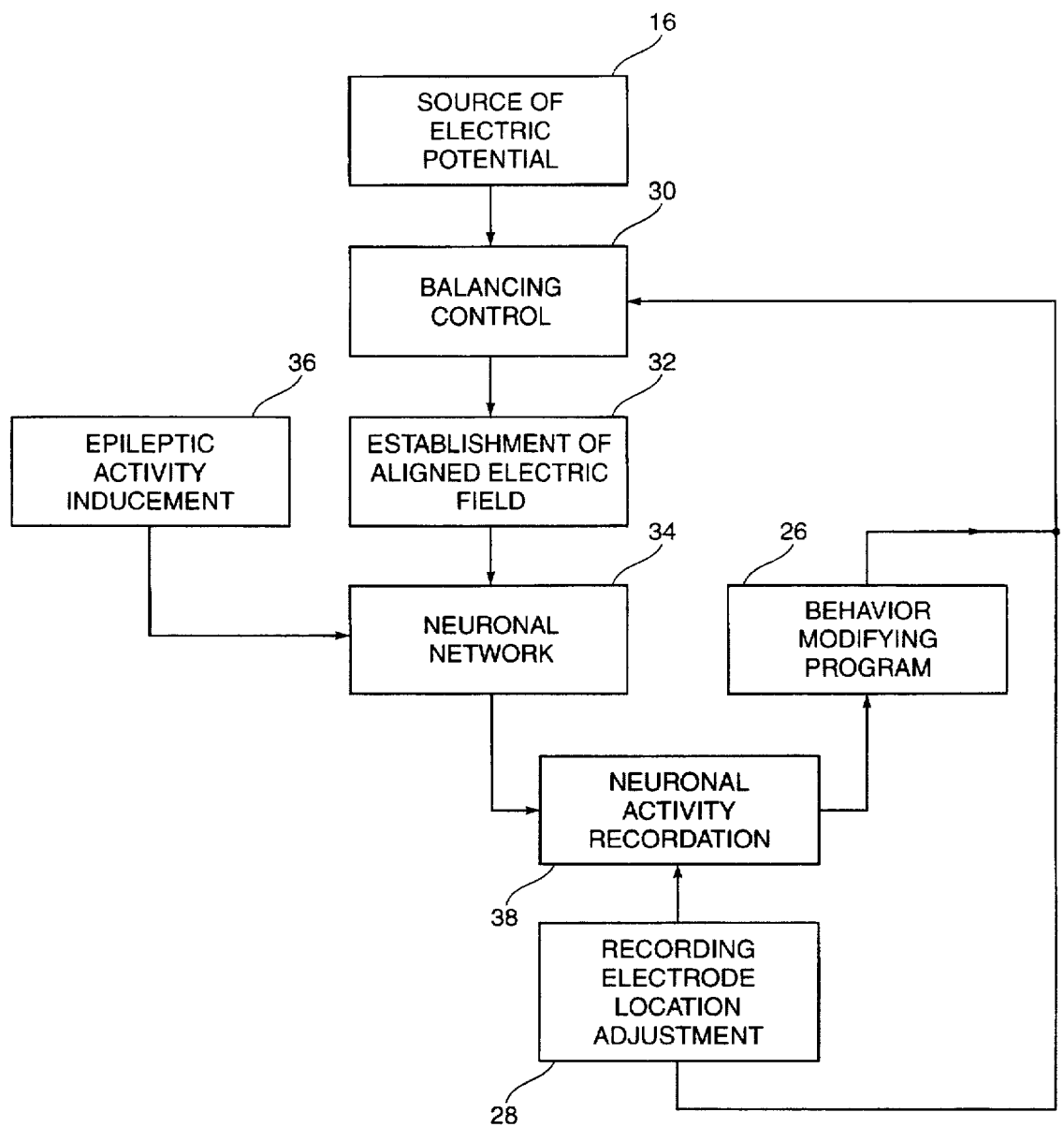
FIG. 3 is a block diagram outlining the activity suppression method associated with the system diagrammed in FIG. 1.

The behavior modifying program denoted by reference numeral 26 in the block diagram of FIG. 3 outlining the activity suppression method hereinbefore described, determines recording electrode location for adjustment 28 and field balancing control 30 of the electric potentials from source 16 as also denoted in FIG. 3. Establishment of the aligned electric field, denoted as 32 in FIG. 3, is thereby achieved with respect to a neuronal network 34 such as that embodied in the brain tissue slice 10 within which epileptic activity occurs spontaneously, or is induced as denoted by reference numeral 36. Such neuronal activity is monitored by recordation 30 through the recording electrodes hereinbefore described to provide an input to the behavior modifying program 26 for control of epileptic focus, thereby suppressing or abolishing epileptic activity through dc electric fields of short duration.

Obviously, other modifications and variations of the present invention may be possible in light of the foregoing teachings. It is therefore to be understood that within the scope of the appended claims the invention may be practiced otherwise than as specifically described.

What is claimed is:

1. A method of modifying behavior of a neural system within which epileptic activity occurs including the steps of: generating an electric field; positioning the electric field in operative alignment with the neural system; and varying magnitude of the operatively aligned electric field in accordance with a chaos controlling algorithm to suppress the epileptic activity in the neural system.

2. The method as defined in claim 1, further including the step of: recording the epileptic activity in the neural system to determine the variation in magnitude of the operatively aligned electric field.

3. The method as defined in claim 1 wherein said step of varying magnitude of the operatively aligned electric field includes balancing positive and negative potentials utilized for establishment of the electric field to minimize change in potential applied to the neural system through the operatively aligned electric field.

4. The method as defined in claim 3 wherein the neural system is embodied in brain tissue having neurons with respect to which the electric field is operatively aligned in parallel relation by said step of positioning the electric field.

5. The method as defined in claim 4 including the step of exposing the brain tissue to a perfusate through which the epileptic activity is induced.

6. The method as defined in claim 1 wherein said step of varying magnitude of the operatively aligned electric field includes balancing positive and negative potentials utilized for establishment of the electric field to minimize change in potential applied to the neural system through the operatively aligned electric field.

7. The method as defined in claim 1 wherein the neural system is embodied in brain tissue having neurons with respect to which the electric field is operatively aligned in parallel relation by said step of positioning the electric field.

8. A method of modifying behavior of a neural system embodied in brain tissue having neurons, including the steps of: exposing the brain tissue to a perfusate for inducing epileptic activity in the neural system; generating an electric field; positioning the electric field in parallel relation to the neurons of the brain tissue for operative alignment with the neural system; and controlling variation in magnitude of the operatively aligned electric field to suppress the epileptic activity in the neural system.

9. A method of modifying behavior of a neural system within which epileptic activity occurs including the steps of: generating an electric field; positioning the electric field in operative alignment with the neural system; recording the epileptic activity in the neural system; and varying the electric field in magnitude dependent on said recording of the epileptic activity in accordance with a chaos controlling algorithm for suppression of said epileptic activity.

10. A method of treating pulsating activity of a neural system, including the steps of: monitoring behavior of the neural system in accordance with a chaos controlling algorithm for identification of neuronal focus of the pulsating activity; and applying an electric field of limited duration to the neural system for suppression of said neural focus of the pulsating activity in response to said identification thereof.

* * * * *